(12) United States Patent
Van Lankvelt et al.

(10) Patent No.: US 8,486,718 B2
(45) Date of Patent: Jul. 16, 2013

(54) MAGNETIC SYSTEM

(75) Inventors: Petrus Johannes Wilhelmus Van Lankvelt, Boekel (NL); Menno Willem Jose Prins, Rosmalen (NL)

(73) Assignee: Koninklijke Philips N.V., Eindhoven (NL)

( * ) Notice: Subject to any disclaimer, the term of this patent is extended or adjusted under 35 U.S.C. 154(b) by 571 days.

(21) Appl. No.: 12/299,792

(22) PCT Filed: May 8, 2007

(86) PCT No.: PCT/IB2007/051719
§ 371 (c)(1),
(2), (4) Date: Nov. 6, 2008

(87) PCT Pub. No.: WO2007/129277
PCT Pub. Date: Nov. 15, 2007

(65) Prior Publication Data
US 2009/0181856 A1    Jul. 16, 2009

(30) Foreign Application Priority Data

May 10, 2006  (EP) .................................. 06113768
Mar. 6, 2007  (EP) .................................. 07103631
Mar. 6, 2007  (EP) .................................. 07103633

(51) Int. Cl.
*G01N 33/543* (2006.01)
*C40B 60/12* (2006.01)

(52) U.S. Cl.
USPC ................ 436/518; 506/9; 506/39; 422/68.1; 335/151; 335/152; 335/153; 335/154; 335/155; 335/156; 335/157; 335/205; 335/206; 335/207; 324/207.11; 324/257

(58) Field of Classification Search
USPC .................. 506/9, 39; 422/68.1; 436/518
See application file for complete search history.

(56) References Cited

U.S. PATENT DOCUMENTS

| 4,211,411 | A  | * | 7/1980 | McDaniel et al. ......... 273/348.3 |
| 4,441,021 | A  | * | 4/1984 | Olson et al. ............. 250/227.11 |
| 5,582,153 | A  | * | 12/1996 | Dutt et al. .................... 123/450 |
| 5,655,665 | A  |   | 8/1997 | Allen et al. |
| 7,046,002 | B1 | * | 5/2006 | Edelstein ..................... 324/244 |
| 2002/0174878 | A1 |  | 11/2002 | Nisson et al. |
| 2005/0284817 | A1 |  | 12/2005 | Fernandez et al. |

FOREIGN PATENT DOCUMENTS

| EP | 0031503 A2 |   | 7/1981 |
| GB | 2304984 A  |   | 3/1997 |
| WO | 0140790    | * | 6/2001 |
| WO | 0216904 A2 |   | 2/2002 |
| WO | 03054566 A1 |  | 7/2003 |

OTHER PUBLICATIONS

Marble A E et al: An analytical methodology for magnetic field control in unilateral NMR Journal of Magnetic Resonance, Academic Press, Orlando, FL, US, vol. 174, No. 1, May 2005, pp. 78-87, XP004833775 ISSN: 1090-7807.

* cited by examiner

*Primary Examiner* — Krishnan S Menon
*Assistant Examiner* — Rebecca M Fritchman

(57) ABSTRACT

A magnetic system for biosensors is switchable between attraction force and repulsion force near the sensor surface. The magnetic system includes a magnetic source and a sensor. The sensor corresponds with the magnetic field in a way that the magnetic source creates inhomogeneous magnetic field lines that results in a magnetic force towards the magnetic system and which subsequently or adjacently exerts a magnetic force directed away from the magnetic system with all magnetic forces generated at the same magnetic source.

14 Claims, 6 Drawing Sheets

MAGNETIC SYSTEM

Figure 1:
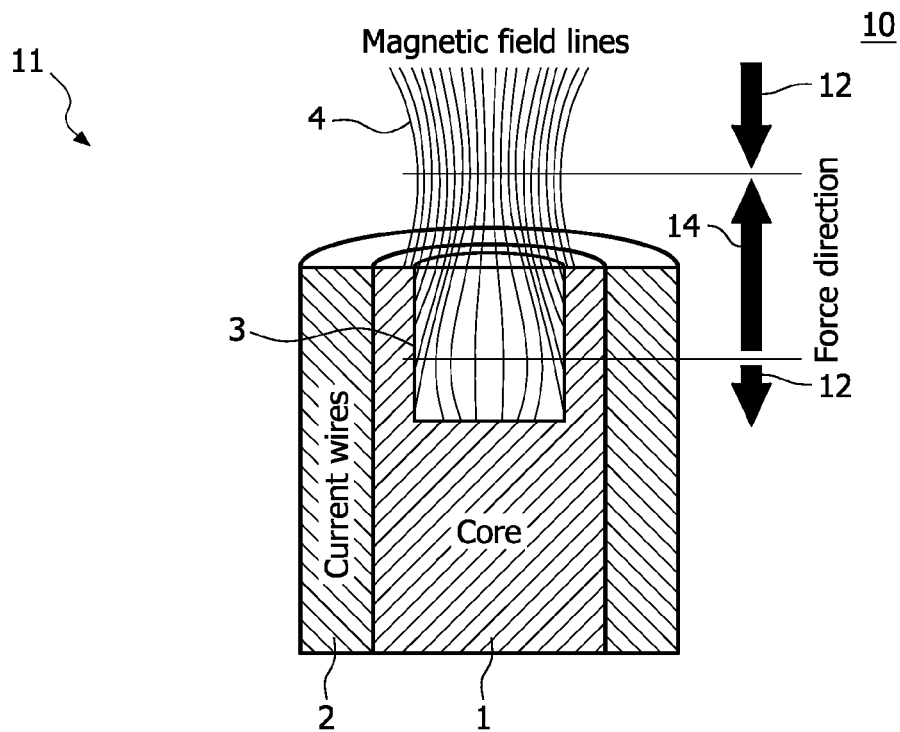

The invention relates to a magnetic system.

For an effective evaluation of biomaterial components, the biomaterial has to be brought into a close contact to the surface of a biosensor. Therefore, an attracting force to the biomaterial must be generated. This is usually realised by magnetic particles or beads, which will be chemically or physically bound to the biomaterial to connect the biomaterial to be examined with a substrate. A magnetic attraction force is generated near the biosensor surface to attract the magnetic beads bound to the biomaterial or biological molecules enclosed therein, respectively.

Magnetic actuation is a promising measuring method for the operation of biosensors. Firstly, it speeds up the concentration and therefore the binding process of the magnetic particles at the sensor surface. Secondly, magnetic washing can replace the traditional wet washing step, which is more accurate and reduces the number of operating actions.

Compared to the chip dimensions, large external electromagnets can be used for actuation in order to achieve homogeneous field gradients at the sensor surface and a large penetration depth over the entire sample volume of biomaterial. These qualities in measuring are hard to achieve with integrated actuation structures.

The biosensors of biochips described have promising properties for biomolecular diagnostics in terms of sensitivity, specificity, integration, ease of use and costs.

Examples of such biosensors or biochips are given in WO 2003054566, which describes the excitation of magnetic beads with uniform magnetic fields.

A biosensor as described here is based on the detection of superparamagnetic beads and may be used to simultaneously measure the concentration of a large number of different biological molecules in a solution of biomaterial.

So, the sensor surface must have a close contact to the biomaterial which can be achieved by bringing the biomaterial very close to the sensor surface with the help of the mentioned magnetic beads. Another requirement is that after measuring the biomaterial must be washed away, in order to condition the sensor surface for the next measurement.

The washing can also be realised by means of the magnetic beads mixed with the biomaterial, thus generating a magnetic repulsion force near the sensor surface.

Normally, a magnetic force induced by a magnet or an electromagnet is directed towards the magnet. Therefore, two magnets are needed for inducing a magnetic force toward the sensor surface, the so called sedimentation, and away from the sensor surface, the so called washing.

It is an object of the present invention, to provide a magnetic system and a method with the aforesaid properties which show an attraction force and a repulsion force. Disclosed is a magnetic system comprising magnetic means to generate a magnetic field which exerts a magnetic force directed towards the magnetic system and which subsequently or adjacently exerts a magnetic force directed away from the magnetic system with all magnetic forces generated at the same source of the magnetic means. The magnetic forces can change in time, a magnetic force in a first zone exists at one time, whereas a magnetic force in the second zone exists at another time. Also, the magnetic forces in the first and the second zone can exist at the same time at different spatial zones or areas. This means, the magnetic forces in the first zone and the second zone exist simultaneously or the magnetic forces exist successively. The magnetic means is designed in anyway, it can comprise one single or a multitude of sources of magnetic power. The term source of the magnetic means therefore does not limit the scope in a way of a single source of magnetic power. The term source in the sense of this invention means the spatial origin of magnetic power rather than the objective physical source of magnetic power. The magnetic means are arranged at one certain place relative to the biosensor to be operated with.

One example considers a magnet which can do it both. Beside a normal attraction force, this magnet is also capable of applying a repulsive force.

Power consumption is a big issue in portable point-of-care applications in connection with examples of the invention. Therefore, it is important to maximize the force that can be generated with an electromagnet. When the special magnetic system disclosed in this invention is used in combination with a common magnet or electromagnet, the magnitude of the magnetic force can be increased substantially. It is also possible to create the same force at much lower currents compared to the situation in which only standard magnets are used.

The main feature in two alternatives of the invention is the opening in the magnetic core, especially also the special shape of the opening. This causes in one alternative a magnetic attraction force near the surface in a defined near distance and a repulsion force on the biomaterial conditioned with the magnetic beads in a more far distance. So it is essential to switch between the magnetic force directions by a single magnetic system, by changing the relative position between magnetic system and sensor surface.

In a second alternative the magnetic system can switch easily between repulsion and attraction force by using a concentric magnetic system which has a multiple layered system of at least two concentric coils or windings and ferromagnetic cores, wherein the inner coil-core-arrangement is shorter than the outer coil-core-arrangement, in order to create the opening at that side where the sensor is located adjacent to the magnetic system. With other words the outer core and coil or winding are raised against the inner core and coil or winding.

The sensor surface must have a close contact to the biomaterial which can be caused by bringing the biomaterial very close to the sensor surface with the help of the mentioned magnetic beads. Magnetic beads connected to biomaterial or parts thereof can be used to force the biomaterial or parts thereof in a certain direction. The washing is used to remove the unbound and non-specific bound beads from the sensor surface for proper end point measurement.

An embodiment of the invention discloses an opening in the magnetic core which is a cylindrical blind hole, and another advantageous opening in the core is a cone shaped hole or opening. Further advantageous cross sections of openings are rectangular or squared.

In all cases inhomogeneous magnetic field lines are induced, which cause in a first zone in a defined distance an attractive force and in second zone in a defined distance a repulsive force. It is to be understood that both force directions are created by magnetic means arranged at one certain place. The attractive force and the repulsive force are generated at one place of origin or source. This is not to be mistaken with a magnetic system arranged at different places, e.g. two sources arranged opposite to each other on different sides of the sensor.

A further embodiment of the invention discloses that the sensor is movable between inside and outside the opening in the core. With other words, the sensor can be driven in both force direction positions. This is essential for the first alternative, where the sensor is movable relatively to the magnetic system.

For the second alternative, no sensor or magnet movement is necessary. A multilayered concentric system according to this second alternative comprises at least two magnetic means, which are coils or permanent magnets. The multilayered concentric system comprises one coil and can comprise one or more permanent magnets. The multilayered concentric system can also be designed of more than one coil and can also be designed of coils without permanent magnets. By using a multilayered concentric system the switching between repulsion and attraction can be generated by applying a current only to one coil. That means, assuming a multilayered concentric system built with an inner coil and an outer coil, attraction force is generated by only applying a current to an inner coil, and repulsion force is generated by only applying a current to an outer coil.

According to the first alternative a further embodiment is that a second magnet is arranged adjacent to the magnet, which are separated over a gap, in which the position of the sensor, that means at least the sensor surface, is movable. This special magnetic system is an intensifying magnetic system generating high magnetic forces.

For the advantageous use for biosensors, an embodiment of the invention discloses that the sensor is an array of several sensors. This results in a very effective sensor with a big resulting sensor surface.

A further embodiment of the invention is that the definable end positions of the sensor movement can be optimized by a magnetic field sensor, which can be moved simultaneously with the sensor, in order to evaluate optimal extremes of the magnetic flux. By this, the magnetic forces generated near the sensor surface can be optimized in their strength in order to generate maximum magnetic force in attraction mode as well as in repulsion mode. This causes an intense contact to the biomaterial in sensing modus, as well as an optimal repulsion in washing modus.

A further object of the invention is solved by a method which uses a magnetic system for biosensors as described, by which a sensing material or liquid is dispersed with or chemically bound to microscopic magnetic beads, and the sensor chip is moved in a close position to the opening in the magnetic core, in order to generate magnetic repulsion near the sensor surface zone to wash the surface by repulsion forces of the magnetic beads, and the sensor chip is moved in a defined distance of the core in order to generate attraction forces to the magnetic beads for sensing the biosubstrate arranged at the sensor in a very close contact to the sensor surface.

By switching between the two distant positions, the mode of operation of the sensor can be changed between an optimized measuring modus and an optimized washing modus.

An embodiment of the method is characterized in that the movement between the sensor or sensor chip and the magnetic core is a relative movement, by which the core is moved in such a way that a first sensor position is placed out of the opening in the magnetic core, being in the influence of the attractive force zone, and another sensor position is inside the opening of the magnetic core, in the influence of the repulsive force zone.

This movement between the sensor or sensor chip and the magnetic core is relative, so moving the sensor chip or moving the coil with the magnet core results in the same relative position towards each other.

A last embodiment of the method is characterized in that in a magnetic arrangement two magnets are separated by a gap, so that the relative position of the sensor is between inside the opening of one magnetic core and inside the gap between the two magnetic cores.

Further, a device incorporating a magnetic system used in one or more of the following applications is disclosed: a biosensor used for molecular diagnostics, the rapid and sensitive detection of proteins and nucleic acids in complex biological mixtures such as e.g. blood or saliva, the high throughput screening devices for chemistry, pharmaceuticals or molecular biology, a testing device e.g. for DNA or proteins e.g. in criminology, for on-site testing, for instance in a hospital or road site testing, for diagnostics in centralized laboratories or in scientific research, a tool for DNA or protein diagnostics for cardiology, infectious disease and oncology, food, and environmental diagnostics, a tool for combinatorial chemistry, an analysis apparatus, a biosensor using optical detection, a biosensor using the piezoelectric effect, especially with electrical charge caused by particles generating heat when illuminated. The invention is also useful for the latter application of a biosensor which uses light absorbing particles as labels. The labels bind to a surface by biological means. When optically illuminated the particles generate heat which in turn generates electrical charge in a piezoelectric film. This charge generated can be detected by electrical means. The invention is especially useful when using magnetic particles as labels in the biosensor described above. Magnetic particles generally have a high content of iron oxide, so that the magnetic particles are strong optical absorbers. Furthermore, magnetic actuation in the biosensor described above allows a rapid transport of labels to the binding surface, the creation of optimal conditions for binding, e.g. using actuation with pulsed forces being effective on the magnetic particles, and it allows a well-controlled separation between the bound and unbound magnetic particles on the sensor surface to reduce background signals from unbound magnetic particles in the bulk and to enhance the biological specificity of the measurement. Further, it allows a control of the timing when the binding to the surface starts, such that offset signals can be subtracted.

Different embodiments of the invention are shown in FIG. 1 to FIG. 9. Additional details, features, characteristics and advantages of the object of the invention are disclosed in the subclaims, the figures and the following description of the respective figure and examples, which in an exemplary fashion show embodiments of the invention.

Figure 2:
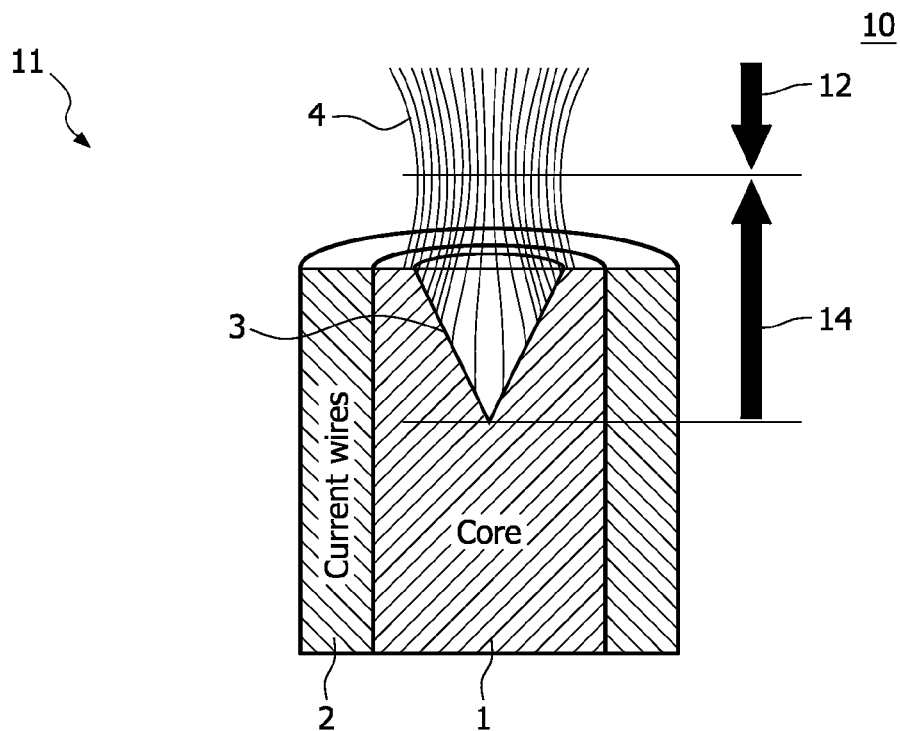
Figure 3:
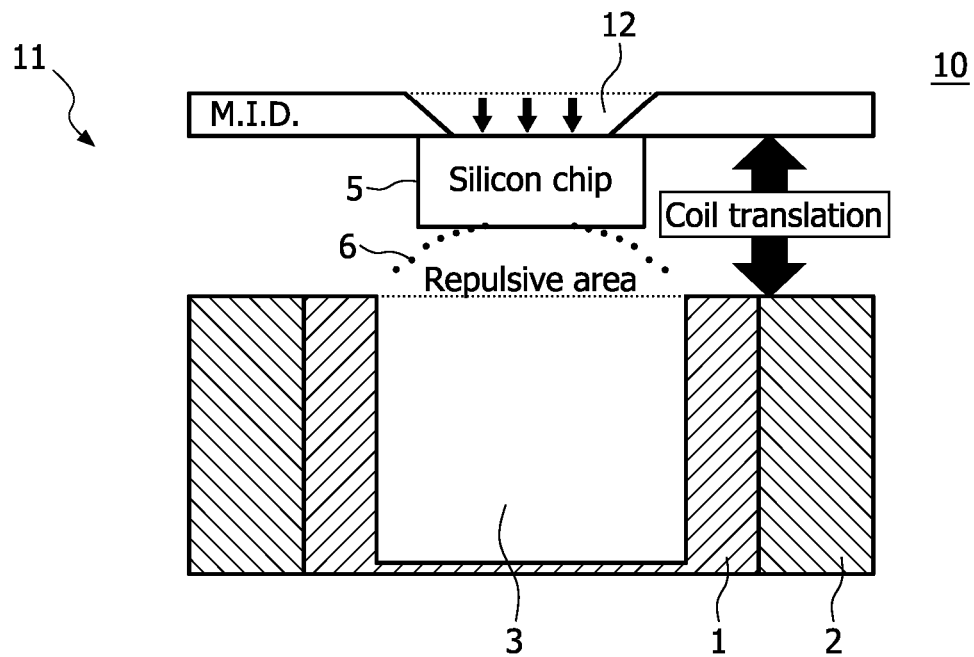
Figure 4:
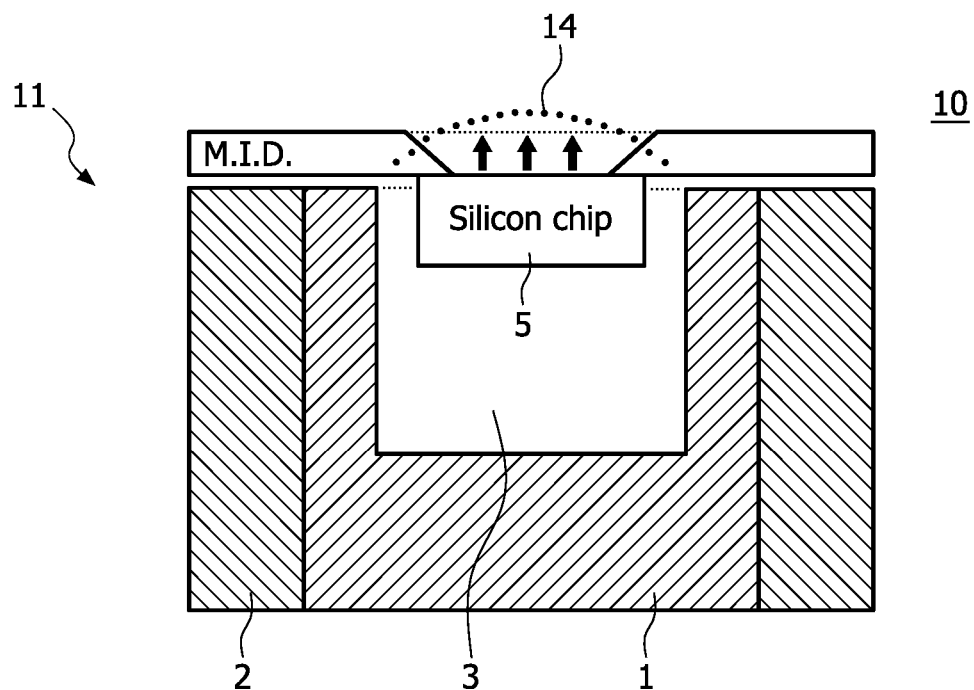
Figure 5:
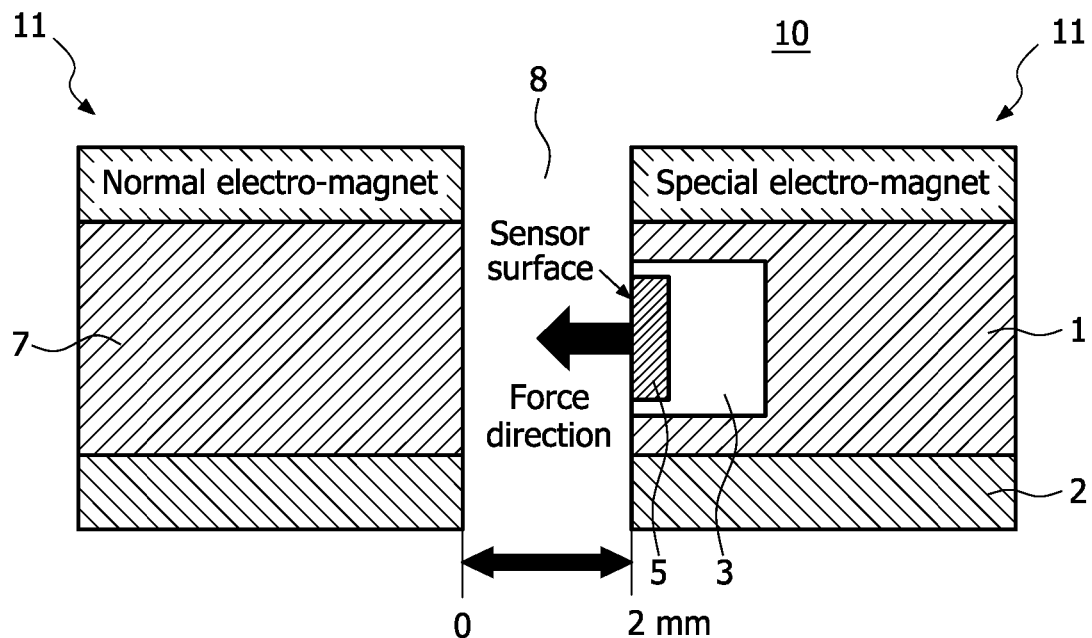
Figure 6:
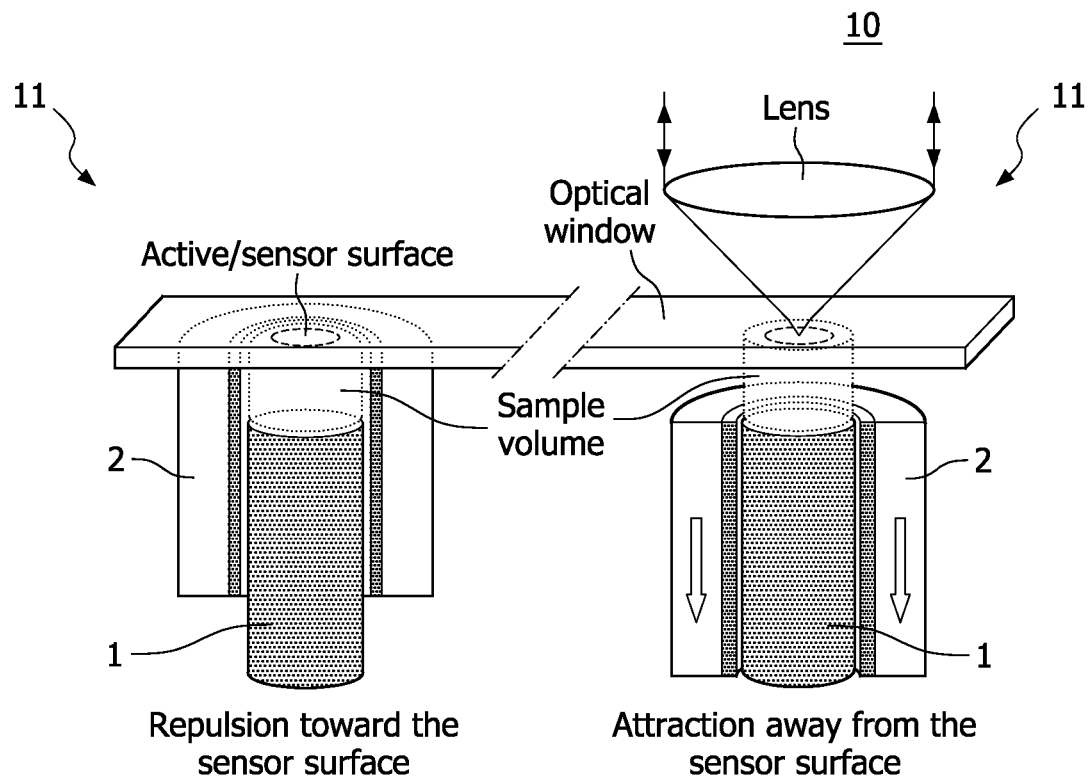
Figure 7:
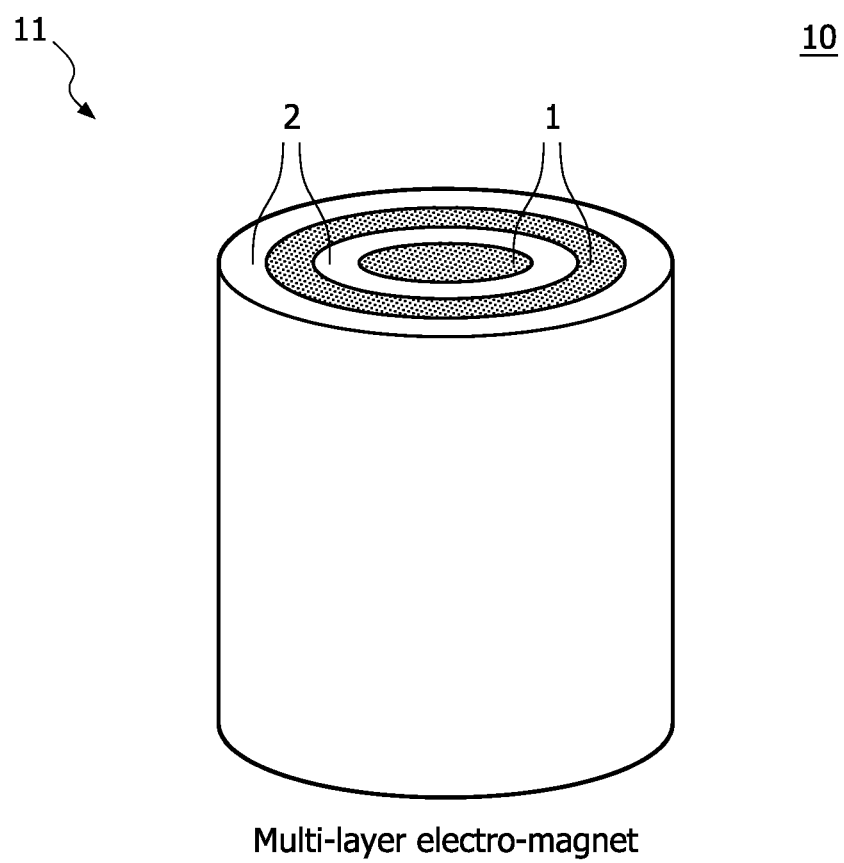
Figure 8:
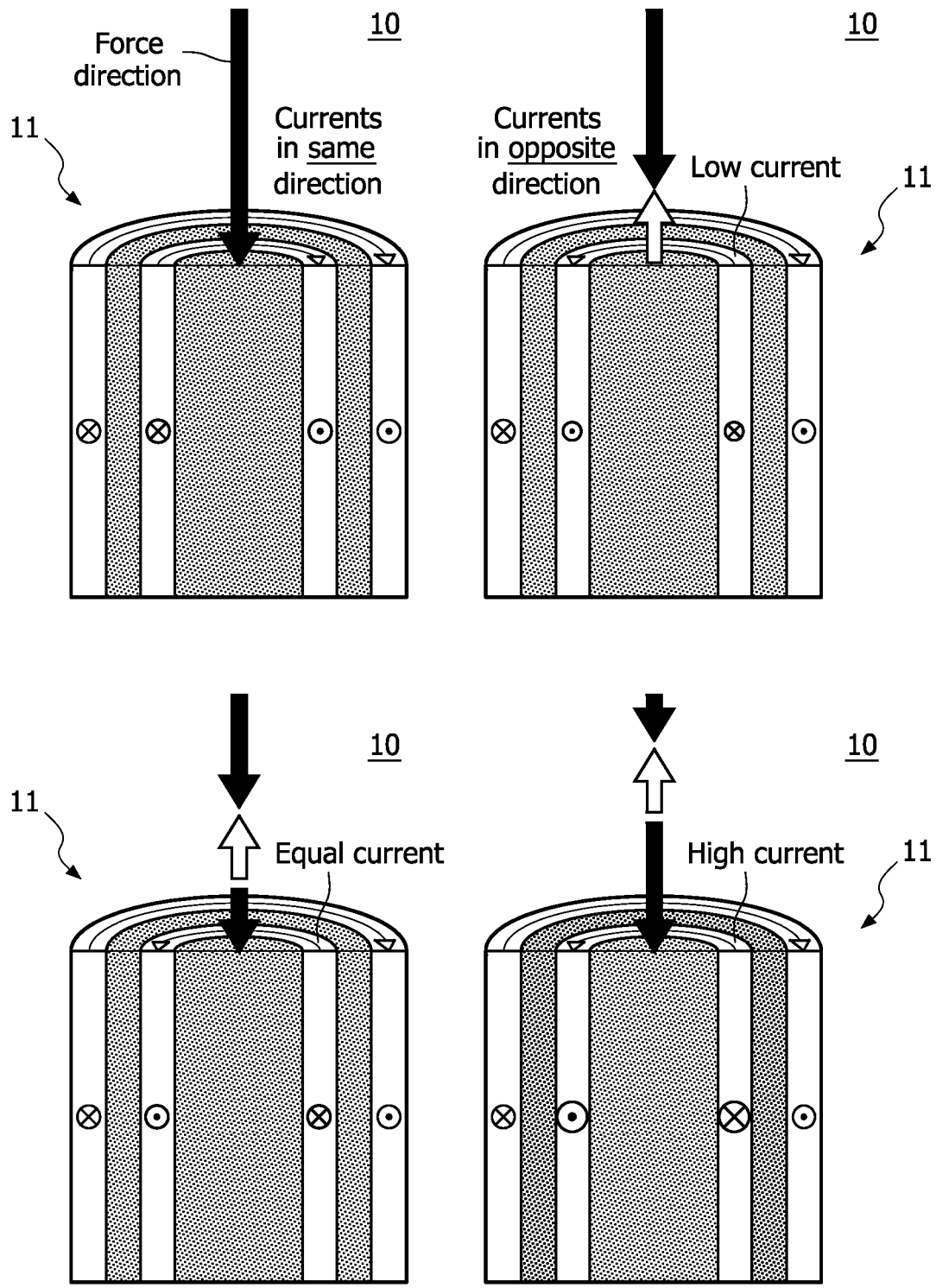
Figure 9:
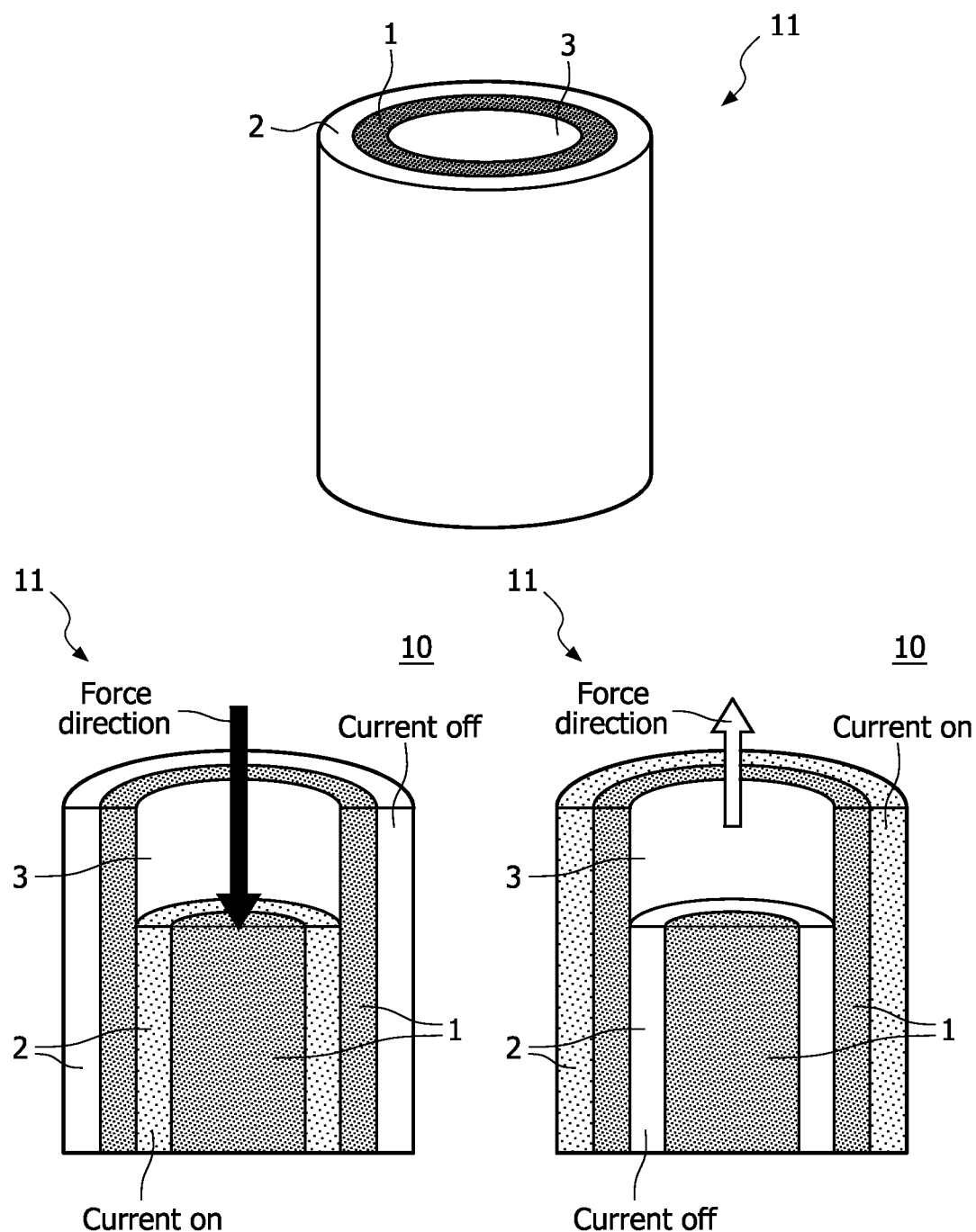

FIG. 1 shows a cross section of first embodiment of a magnetic system with a core having a cylindrical opening surrounded by a coil, FIG. 2 shows a further embodiment similar to FIG. 1 with a cone shaped opening instead of a cylindrical opening, FIG. 3 shows a cross section similar to FIG. 1 with a sensor above the opening in the core moved in a position above the opening, FIG. 4 shows a cross section similar to FIG. 3 with a sensor moved in a position within the opening in the core, FIG. 5 shows a cross section similar to FIG. 4 with the magnetic means and sensor tilted and an additional electromagnet arranged next to the magnetic means, FIG. 6 shows a schematic side view of a magnetic means comprising a core with coil and a sensor, whereby the sensor is scanned by optical means, FIG. 7 shows an elevated view of a magnetic means build up by alternating cores and coils surrounding the cores concentrically, FIG. 8 shows four cross sections similar to FIG. 7 with one core and coil lowered regarding the other core and coil and with different current directions flowing through the cores and coils and accordingly different states of magnetisation of the magnetic means, with first zones above the magnetic means in which a magnetic force directed towards the magnetic system is exerted and with second zones above the magnetic means in which a magnetic force directed away from the magnetic system is exerted, FIG. 9 shows three views similar to FIG. 8 of a multilayered magnetic system with shifted inner portion, an upper elevated view and two elevated cut views below, whereby an inner core with coil is shifted relatively to the outer core with coil and has a smaller length.

FIG. 1 shows a first embodiment of the invention of a magnetic system 10 with a core 1 having a cylindrical opening 3 surrounded by a coil 2, denoted in FIG. 1 as current wires. Here, the opening 3 in the magnetic core 1 has a cylindrical shape. In contrast to a core 1 without an opening 3, e.g. with a plane surface for the output of magnetic field lines which can only cause an attractive magnetic force, the cylindrical opening 3 causes such an inhomogeneous magnetic field, represented by the magnetic field lines 4, that in dependency to the distance from the bottom of the opening 3 below towards outwards the magnetic core 1, the effected magnetic force changes its direction two times, as indicated by the three arrows directed in alternating directions. The three arrows characterize the different zones 12, 14 in FIG. 1, the first zone 12 exerting a magnetic force directed towards the magnetic system 10 characterized by the arrows directed downwards and the second zone 14 exerting a magnetic force directed away from the magnetic system 10 characterized by the arrows directed upwards. In this example two first zones 12 exist above and below one second zone 14. So, in dependency of the actual relative sensor positions (not shown), which can be changed mechanically, the sensor 5 can be shifted into the attractive force zone, the first zone 12, or into the repulsive force zone, the second zone 14, of the magnetic field of the magnetic system 10.

The sensor 5 can be any suitable sensor 5 to detect the presence of magnetic particles on or near to the sensor surface, based on any property of the particles, e.g. it can detect via magnetic methods, e.g. magnetoresistive, Hall, coils 2. The sensor 5 can detect via optical methods, for example imaging, fluorescence, chemiluminescence, absorption, scattering, surface plasmon resonance, Raman spectroscopy etc. Further, the sensor 5 can detect via sonic detection, for example surface acoustic wave, bulk acoustic wave, cantilever deflections influenced by the biochemical binding process, quartz crystal etc. Further, the sensor 5 can detect via electrical detection, for example conduction, impedance, amperometric, redox cycling, etc. and any combinations thereof.

FIG. 2 shows another embodiment, in which the opening 3 in the core 1 is cone shaped. This special shape of the opening 3 causes a magnetic field in which the magnetic force is strongly repulsive and at another distance from the core 1 in which it is attractive. In FIG. 2 the arrow above characterizes the first zone 12 in which a magnetic force is directed downwards, the arrow below characterizes the second zone 14 in which a magnetic force is directed upwards. In this arrangement two zones 12, 14 are given, one first zone 12 and one second zone 14. This special shape of the opening 3 in FIG. 2 causes a greater repulsion force than the cylindrical opening 3 shown in FIG. 1.

In both embodiments shown in FIG. 1, FIG. 2, only one coil 2 is needed for both attracting the magnetic beads for sedimentation, and repelling of the magnetic beads for washing. Just only by translation of the coil 2 or the sensor 5 (not shown), the actual magnetic force can be switched between attractive force and repulsive force.

FIG. 3 and FIG. 4 show cross sections similar to FIG. 1 with a sensor 5 above the opening 3 in the core 1 moved in a position above the opening 3. Shown are the two end positions of the sensor 5 or sensor chip movement. In FIG. 3 the status is demonstrated, in which the sensor 5 or the coil 2 within the magnetic core 1 is mechanically translated for a defined relative distance, so that the second zone 14, the repulsive zone, of the magnetic system 10 ends below the sensor 5, so that the first zone 12 above the sensor 5 is influenced by the attractive magnetic force. The attractive force is denoted by three arrows above the sensor 5 directed downwards. So the magnetic force in this first zone 12 attracts the magnetic beads in the biomaterial to be examined in order to speed up the sedimentation of magnetic beads on the sensor surface.

In FIG. 4 is shown the other relative end position of the sensor 5, where the sensor 5 resides inside the opening 3, so that the repulsive second zone 14 is situated above the sensor 5. In this position a repulsive force on the magnetic beads in the biomaterial is generated, so that it is repelled, or in other words, washed away from the sensor surface quickly. The repulsive force is denoted by three arrows above the sensor 5 directed upwards.

The magnitude of the magnetic force is very important for the desired effect of sedimentation and washing. The force is linear proportional to the speed of the magnetic beads and therefore also to the sedimentation time. More important is that a certain force has to be overcome in order to wash away the non specific beads from the surface.

FIG. 5 shows a cross section similar to FIG. 4 with the magnetic means 11 designed as core 1 and coil 2 and sensor 5 tilted. An additional second coil 7 is arranged adjacent to the magnetic means 11, which is hereby designed as an electromagnet. Using a second coil 7 can boost the magnetic force.

This second coil 7 is a normal coil additional to the special coil 2 described above, between which the gap 8 is arranged. In this example the distance between the core 1 with coil 2 and the second coil 7 is 2 mm. The sensor 5 is moved inside this gap 8, alternatively the core 1 with coil 2 is translated with the same resulting effect. The effective force, using both electromagnetic coils 2, 7, is boosted by a factor of nearly four compared to the magnetic system 10 using only one single coil 2. Compared to a magnetic system 10 that uses only a single conventional coil, a boosting factor of more than ten is achieved.

This boosting property of the magnetic system 10 has some major benefits. Less current is needed in order to achieve the same amount of force. By this, the magnetic system 10 can be sustained with less or even without active cooling of the coils 2, 7. Less current and less active cooling saves a lot of power, which is for example very important for portable point-of-care applications of the sensor 5 or biosensor.

As stated above the sensor 5 can be any suitable sensor 5 to detect the presence of magnetic particles on or near to a sensor surface, based on any property of the particles, e.g. it can detect via magnetic methods for example magnetoresistive methods, Hall methods, coils 2, 7 etc, as well as optical methods like imaging, fluorescence, chemiluminescence, absorption, scattering, surface plasmon resonance, Raman, etc. Also sonic detection is possible, that means generation and detection of surface acoustic wave, bulk acoustic wave, cantilever, quartz crystal etc, as well as electrical detection like conduction, impedance, amperometric, redox cycling, etc.

The labels can be detected directly by the sensing method described. As well, the particles can be further processed prior to detection. An example of further processing is that materials are added or that the chemical, biochemical or physical properties of the label are modified to facilitate detection.

The detection can occur with or without scanning of the sensor 5 with respect to the biosensor surface. In addition to molecular assays, also larger moieties can be detected, e.g. cells, viruses, or fractions of cells or viruses, tissue extract, etc.

Measurement data can be derived as an end-point measurement, as well as by recording signals kinetically or intermittently.

The device and method can be used with several biochemical assay types, e.g. binding/unbinding assay, sandwich assay, competition assay, displacement assay, enzymatic assay, etc.

The magnetic system 10 and method of this invention are suited for sensor multiplexing, for example the parallel use of different sensors 5 and sensor surfaces, label multiplexing for example the parallel use of different types of labels, and chamber multiplexing for example the parallel use of different reaction chambers incorporating sensing material to be measured.

The magnetic system 10 and methods described in the present invention can be used as rapid, robust, and easy to use point-of-care sensor 5 or biosensor for small sample volumes. The reaction chamber can be a disposable item to be used with a compact reader, containing the one or more magnetic field generating means and one or more detection means. Also, the magnetic systems 10 and the method described can be used in automated high-throughput testing. In this case, the reaction chamber is e.g. a well plate or cuvette, fitting into an automated instrument.

FIG. 6 shows optical means for the aforesaid optical or optoelectronical detection. Optical labels offer some desirable properties:

- Many detection possibilities like imaging, fluorescence, absorption, scattering, turbidometry, SPR, SERRS, luminescence, chemiluminescence, electrochemiluminescence, FRET, etc.
- Imaging possibility offers high multiplexing.
- Optical labels are generally small and do not influence the assay too much.

A good combination would be to use magnetic labels that can be actuated by applying magnetic field gradients and that can be detected optically. An advantage is that optics and magnetics are orthogonal in the sense that in most cases optical beams do not show interference with magnetic fields and vice versa. This means that magnetic actuation would be ideally suited for combination with optical detection. Problems such as sensor disturbance by the actuation fields are eliminated.

The problem of combining magnetic actuation and optical detection is in the geometrical constraint. To develop a cartridge technology that is compatible with magnetic actuation means, typically an electromagnet needs to operate at a small distance between magnet and sensor surface. An optical system needs to scan the same surface, possible with high-NA optics. The optomechanical set up and the electromagnet therefore hinder each other when integrating a concept with magnetic actuation and optical detection. Preferably, a configuration with a magnetic means 11 on only one side is needed. This magnetic means 11 is able to generate a switchable magnetic field.

For the second alternative FIG. 7 shows a drawing of a multilayered electromagnet. A multilayered concentric system according to this second alternative comprises at least two magnetic means, which are coils 2, also referred to as windings, or permanent magnets. The multilayered concentric system comprises one coil 2 and can comprise one or more permanent magnets. The multilayered concentric system can also be designed of more than one coil 2 and can also be designed of coils 2 without permanent magnets. The electromagnet in example shown consists of two separate layers of winding or coils 2 and two layers of core material. By varying the magnitudes and directions of the different currents through both windings, the magnetic field can be deformed. This deformation makes this electromagnet useful for many different applications without using any mechanical step.

FIG. 8 shows four cross sections similar to FIG. 7 with one inner core 1 and coil 2 lowered regarding the other outer core 1 and coil 2. This means the length of the inner core 1 and coil 2 differ from the outer core 1 and coil 2. The four cross sections have different current directions flowing through the cores 1 and coils 2 characterized by the bended arrows along the coils 2. The lengths of the arrows directed towards and away from the magnetic means 11 indicate the ratio of the magnetic forces. In the left upper cross section the currents both run clockwise in both coils 2. In this example the two currents are essentially equal. This leads to a magnetic force direction directed downwards towards the magnetic means 11, indicated by the arrow directed downwards. In the right upper cross section one current in the outer coil 2 runs clockwise and one current in the inner coil 2 runs anticlockwise. In this example the two currents are not equal in strength, the current through the outer coil 2 is higher than the current through the inner coil 2. This leads to a magnetic force direction directed upwards near the magnetic means 11 indicated by the arrow directed upwards and also to another magnetic force direction far from the magnetic means 11 directed downwards towards the magnetic means 11, indicated by the arrow directed downwards opposite to the other arrow. The magnetic force near to the magnetic means 11 is hereby lower than the current far from the magnetic means 11, indicated by the ratio of arrow lengths.

In the left lower cross section one current in the outer coil 2 runs clockwise and one current in the inner coil 2 runs anticlockwise. In this example the two currents are essentially equal in strength. This leads to a first magnetic force direction directed downwards near the magnetic means 11 indicated by the arrow directed downwards, to a second magnetic force direction far from the magnetic means 11 directed upwards away from the magnetic means 11, indicated by the arrow directed upwards opposite to the other arrow. Further, the magnetic means 11 arranged in the described way of FIG. 8, left lower cross section, a third force direction is directed downwards in an zone more distant from the magnetic means 11 indicated by the arrow directed downwards most distant from the magnetic means 11. The magnetic force near to the magnetic means 11 is hereby similar to the opposite magnetic force more far from the magnetic means 11. The magnetic force most distant to the magnetic means 11 is hereby higher than the other two magnetic forces. In the right lower cross section one current in the outer coil 2 runs clockwise and one current in the inner coil 2 runs anticlockwise. In this example the two currents are not equal in strength, the current through the outer coil 2 is smaller than the current through the inner coil 2. This leads to a first magnetic force direction directed downwards near the magnetic means 11 indicated by the arrow directed downwards, to a second magnetic force direction far from the magnetic means 11 directed upwards away from the magnetic means 11, indicated by the arrow directed upwards opposite to the other arrow. Further, the magnetic means 11 arranged in the described way of FIG. 8, right lower cross section, a third force direction is directed downwards in an zone more distant from the magnetic means 11, indicated by the arrow directed downwards most distant from the magnetic means 11. The nearest magnetic force to the magnetic means 11 is hereby higher than the other two magnetic forces which are similar to each other.

When both currents flow in the same direction, the magnetic means 11 has a common electromagnet behaviour, as shown in the left upper cross section of FIG. 8. When both currents flow in opposite directions, a repulsive second magnetic force zone 14 is created, as shown by the upward arrows directed away from the magnetic means 11 in the right upper cross section, left lower cross section, and right lower cross section of FIG. 8. The position of this second zone 14 can be tuned by varying the amplitude of both currents with respect to each other.

This embodiment shown in the four cross sections of FIG. 8 describes a manner to use the multi layered magnetic means 11, in this example an electromagnet, as shown in FIG. 7. This multi layered electromagnet acts like a normal electromagnet when the currents through both coils 2 or layers of winding flow in the same direction. This normal electromagnet behaviour is shown in FIG. 8, left upper view. Starting from this, by changing the direction of one of the currents, for example the current of the inner coil 2, the shape of the magnetic field will be affected and the changed field gradient creates a certain second zone 14 where the magnetic force is directed away from the magnetic means 11. This principle is shown in FIG. 8, right upper cross section, left lower cross section, and right lower cross section. By changing the amplitude of both currents with respect to each other, the position of this repulsive second zone 14 can be tuned. If the inner current is small compared to the other current, the repulsive second zone 14 is just above the surface of the magnetic means 11, as shown in FIG. 8, right upper view. By increasing this inner current with respect to the outer current, the repulsive second zone 14 is shifted up, as shown in FIG. 8, lower two views. This phenomenon can apply a repulsive magnetic force in an a zone that is not in close contact with the magnetic means 11. This becomes important if spacing between the sensor surface and the magnetic means 11 is large due to a relative thick or robust cartridge for example.

FIG. 9 shows three views similar to FIG. 8 of a multilayered magnetic system 11. Again, an outer core 1 with coil 2 and an inner core 1 with coil 2 is are shown. In comparison to FIG. 8 the inner coil 1 and core 2 have a lower height, are more shifted in relation to the outer coil 1 and core 2, and thus a hole 3 is formed in the magnetic means 11 in axial direction extending through a part of the magnetic means 11. The left elevated cut view below of FIG. 9 clarifies this structure. In this example the current through the outer coil 2 is turned off, the current through the inner coil 2 is turned on. The structure of this magnetic means 11 in combination with the flow of currents described yields a magnetic field which causes a force as indicated by the arrow directed downwards. The direction of the magnetic force in this example is towards the magnetic means 11, which means an attractive force is generated.

The right elevated cut view of FIG. 9 shows the same structure as the adjacent left elevated cut view. There, the current through the outer coil 2 is turned on contrary to the previous example, the current through the inner coil 2 is turned off or is also turned on as in the latest example. The structure of this magnetic means 11 in combination with the flow of currents described yields a magnetic field which causes a force as indicated by the arrow directed upwards. The direction of the magnetic force in this example is away from the magnetic means 11, which means a repulsive force is generated.

By placing the sensor 5 inside or near to the hole 3 of the magnetic means 11 and turning on the current through the outer layer of windings or coils 2, an attractive or repulsive force is exerted to the sensor 5 respectively.

This embodiment of FIG. 9 does not need any movement of the sensor 5 or the magnetic means 11. Instead of moving the sensor 5 the magnetic force direction is switched by turning off the current through the outer windings or coils 2 and by turning on the current through the inner windings or coils 2, as shown in the right lower view of FIG. 9.

This inner structure acts like a normal electromagnet and induces a normal attractive magnetic force.

According to the special embodiment of FIG. 6, it is clear that this can advantageously be used in both alternatives, that means with a magnetic system 10 as described and with a multilayered concentric magnetic system 10.

Although the description refers to an application to sensors related to analyzing of biomaterial the magnetic system 10 described is suitable for any technical field in the context of exerting magnetic forces to items susceptible to it, in which technical field magnetic forces of different directions are applicable.

The particular combinations of features in the above detailed embodiments are exemplary only; the interchanging and substitution of these teachings with other teachings in this and the patents/applications incorporated by reference are also expressly contemplated. As those skilled in the art will recognize, variations, modifications, and other implementations of what is described herein can occur to those of ordinary skill in the art without departing from the spirit and the scope of the invention as claimed. Accordingly, the foregoing description is by way of example only and is not intended as limiting. The scope of the invention is defined in the following claims and the equivalents thereto. Furthermore, reference signs used in the description and claims do not limit the scope of the invention as claimed.

The invention claimed is:

1. A magnetic system comprising a sensor and a magnetic source configured to generate a magnetic field which exerts a magnetic force directed towards the sensor and to subsequently or adjacently exert a magnetic force directed away from the sensor with all magnetic forces generated at the same magnetic source, wherein the magnetic source includes a core and a coil surrounding the core, wherein the core includes an opening which is surrounded by at least one turn of the coil, wherein the coil including the opening is configured to produce inhomogeneous magnetic field lines having an increased local density near the opening, wherein the sensor is located at a side of the core having the opening.

2. The magnetic system according to claim 1, wherein the magnetic source is configured to induce inhomogeneous magnetic field lines to create a first zone and a second zone.

3. The magnetic system according to claim 1, wherein the opening is a blind hole having a cylindrical cross section.

4. The magnetic system according to claim 1, wherein the opening in the core is a cone shaped hole.

5. The magnetic system according to claim 1, wherein the opening in the core has a rectangular or a squared cross section.

6. The magnetic system according to claim 1, wherein the opening is a hole that extends all the way through the coil.

7. The magnetic system according to claim 1, wherein the sensor is movable with respect to the opening.

8. The magnetic system according to claim 1, wherein the magnetic source comprises multiple layers including of at least two concentric cores and two concentric coils.

9. The magnetic system according to claim 1, further comprising a second magnet adjacent to the magnetic source.

10. The magnetic system according to claim 9, wherein the magnetic source and the second magnet are separated over a gap, wherein the sensor is movable in the gap.

11. The magnetic system according to claim 1, wherein the sensor is an array of several sensors.

12. The magnetic system according to claim 1, wherein the at least two definable positions are optimized by a magnetic field sensor, which can be moved simultaneously with the sensor in order to evaluate optimal extremes of the magnetic field.

13. The magnetic system according to claim 1, further comprising magnetic flux guiding material having a substantially higher permeability than a surrounding medium.

14. The magnetic system according to claim 1, wherein the sensor is movable during operation of the magnetic system between at least two definable operating positions of the magnetic system.

* * * * *